United States Patent [19]

Crivello

[11] Patent Number: 5,484,950
[45] Date of Patent: Jan. 16, 1996

[54] PROCESS FOR SELECTIVE MONOADDITION TO SILANES CONTAINING TWO SILICON-HYDROGEN BONDS AND PRODUCTS THEREOF

[75] Inventor: James V. Crivello, Clifton Park, N.Y.

[73] Assignee: Polyset Company, Inc., Mechanicville, N.Y.

[21] Appl. No.: 993,689

[22] Filed: Dec. 21, 1992

[51] Int. Cl.[6] .................. C07D 303/02; C07F 7/08; C07F 7/10; C07F 7/18
[52] U.S. Cl. .................. 549/215; 556/449; 556/434; 556/415; 556/439; 556/436; 556/425; 556/428; 556/445
[58] Field of Search .................. 549/215; 512/449, 512/434, 415, 439, 436, 425, 428, 445

[56] References Cited

U.S. PATENT DOCUMENTS

| | | | |
|---|---|---|---|
| 3,159,601 | 12/1964 | Ashby | 260/46.5 |
| 3,220,972 | 11/1965 | Lamoreaux | 260/46.5 |
| 3,715,334 | 2/1973 | Karstedt | 260/46.5 |
| 4,011,247 | 3/1977 | Sato et al. | 549/215 X |
| 4,082,726 | 4/1978 | Mine et al. | 549/215 X |
| 4,788,268 | 11/1988 | Lau et al. | 549/215 X |
| 4,803,244 | 2/1989 | Umpleby | 525/105 |
| 4,804,768 | 2/1989 | Quirk et al. | 549/215 |
| 4,954,580 | 9/1990 | Zahir | 549/215 X |
| 4,977,198 | 12/1990 | Eckberg | 549/215 X |
| 5,096,990 | 3/1992 | Takayanagi et al. | 528/15 |
| 5,097,054 | 3/1992 | Yamamoto et al. | 556/451 |
| 5,169,962 | 12/1992 | Crivello et al. | 549/215 |
| 5,183,912 | 2/1993 | Okawa | 549/215 X |
| 5,260,455 | 11/1993 | Eckberg | 549/215 |
| 5,332,797 | 7/1994 | Kessel et al. | 549/215 X |

FOREIGN PATENT DOCUMENTS

| | | |
|---|---|---|
| 0388005 | 9/1990 | European Pat. Off. . |
| 0423688A2 | 11/1990 | European Pat. Off. . |
| 01-172391 | of 1989 | Japan . |

OTHER PUBLICATIONS

"(PPh$_3$)$_3$RhCl–Catalyzed Hydrosilylation of Unsaturated Molecules by 1,2Bis (dimethylsilyl)ethane: Unprecedented Rate Difference Between Two Si–H Bonds" Nagashima et al. *Organometallics* 8, 2495–2496 (1989).

*Primary Examiner*—Paul F. Shaver
*Attorney, Agent, or Firm*—Heslin & Rothenberg

[57] ABSTRACT

A process for the selective monoadditon of an olefin or acetylene to a siloxane which contains two reactive Si—H bonds to produce a product in which only one of the two Si—H functions has added across the olefin or acetylene is disclosed. A process for making unsymmetrical siloxanes from symmetrical dihydrosiloxanes and products of both of these processes are also disclosed. Products are represented by the formula I in which $R^1$ and $R^4$ are different:

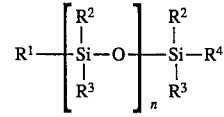

21 Claims, No Drawings

5,484,950

PROCESS FOR SELECTIVE MONOADDITION TO SILANES CONTAINING TWO SILICON-HYDROGEN BONDS AND PRODUCTS THEREOF

Statement of Rights Under Federally Sponsored Research

This invention was made with support under NASA Grant No. NAG-1-980. Accordingly, the U.S. Government may have certain rights in the invention.

BACKGROUND OF THE INVENTION

1. Field of the Invention

The invention relates to a process for the selective monoaddition of an olefin or acetylene to a siloxane which contains two reactive Si—H bonds to produce a product in which only one of the two Si—H functions has added across the olefin or acetylene. The invention also relates to a process for making unsymmetrical siloxanes from symmetrical dihydrosiloxanes and to the products of these processes.

2. Information Disclosure

A major goal in organic and polymer chemistry is to devise methodologies which would enable one to carry out highly specific reactions at one reactive site within a molecule, while at the same time leaving other potentially reactive sites unreacted. Of particular interest to polymer chemistry is the synthesis of molecules which have two different reactive sites for polymerization. Such molecules are highly sought after, since they can be used to prepare a wide variety of reactive intermediates, oligomers and polymers.

The hydrosilylation reaction is well known in the chemical literature and consists of the addition of a Si—H compound across a double or triple bond. For example, the addition of a trialkyl silane to an olefinic double bond as depicted in the equation shown below, results in the formation of a new carbon-silicon bond.

$$R_3Si-H + CH_2=CH-R^1 \xrightarrow{\text{catalyst}} R_3Si-CH_2-CH_2-R^1$$
$$+$$
$$\underset{\underset{R_3Si}{|}}{CH_3-CH-R^1}$$

Traditionally, platinum, palladium, rhodium, cobalt, iridium and iron complexes have been used as catalysts in this reaction. The hydrosilylation reaction is an exceptionally useful reaction which has been employed for the synthesis of a wide variety of interesting intermediates. For example, Lien et al. (U.S. Pat. No. 4,156,046) and Anderson et al. (U.S. Pat. No. 4,304,806) disclose the condensation of trialkoxysilanes with epoxides containing double bonds to obtain compounds which can be used to produce hard, protective coatings for films, negatives and optical discs.

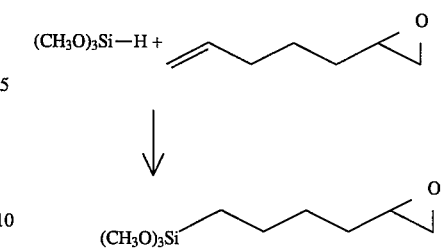

Umpleby (U.S. Pat. No. 4,803,244) discloses the hydrosilylation of an unsaturated elastomer containing multiple carbon-carbon double bonds with a poly(hydrosilane) in the presence of a saturated thermoplastic polymer to produce a thermoplastic elastomer useful for the manufacture of pipes, tubing and fiber optic, wire and cable coating.

Takayanagi et al. (U.S. Pat. No. 5,096,990) disclose the reaction of a divinylpolysiloxane with a dihydropolysiloxane and a poly(hydrogensilane) in the presence of a platinum catalyst to produce resin compositions suitable for coating semiconductor chips.

These and other references which discuss the use of poly(hydrosilanes) for hydrosilylation all produce polysilylated products in which no attempt is made to induce selective reaction with a single Si—H bond in a molecule having multiple Si—H bonds. On the contrary, the usual goal is to "olefinate" as high a proportion of Si—H groups as possible.

Nakos et al. (European Appln 388,005) disclose the selective hydrosilylation of vinyl-functional norbornenes. As in the cases described above, all the Si—H bonds are reacted; however, in the case of the Nakos disclosure, subsets of carbon-carbon double bonds are selectively hydrosilylated.

Nagashima et al. [*Organometallics* 8, 2495–2496, (1989)] disclose that 1,2-bis (dimethylsilyl) ethane undergoes anomalously rapid hydrosilylation to form a monohydrosilyladduct and that the addition of a second mole proceeds at a normal rate. They attributed this phenomenon to the formation of a cyclic bidentate ligand with the catalyst:

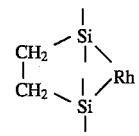

and supported this explanation with the observation that when two more methylenes were interposed [i.e. 1,4-bis-(dimethylsilyl)butane], there was no acceleration of the initial addition. Compounds having more than three atoms between the silicons would not be expected to exhibit any selectivity because the formation of the requisite cyclic structure is not favored.

There thus remains a need for a method for carrying out selective olefination of a single Si—H bond in siloxane polymers containing two such bonds. This would allow easy access to a whole host of differentially functionalized silanes that could then be used as intermediates for the synthesis of useful polymers.

SUMMARY OF THE INVENTION

It is an object of the present invention to provide a process for the selective reaction of a single Si—H bond in a siloxane polymer containing two such bonds.

It is a further object to furnish unsymmetrically substituted reactive monomers, oligomers and polymers of defined structure from dihydro (polysiloxanes).

It is a further object to furnish novel polysiloxanes having useful properties for coatings.

These and other objects, features and advantages are provided by the present invention which comprises a process for selectively reacting one equivalent of an olefin or acetylene with a hydrosilane having two silicon-hydrogen bonds. The process comprises combining one equivalent of a polysiloxane with one to two equivalents of the olefin or acetylene at 20° to 85° in the presence of a platinum, palladium, rhodium, iridium, iron, cobalt or nickel catalyst. The process unexpectedly produces less than 5% of a product incorporating two moles of the olefin or acetylene. The preferred catalyst is a rhodium catalyst, most preferably tris(triphenylphosphine)rhodium (I) chloride.

In another aspect the invention relates to a process for producing an unsymmetrically substituted siloxane from a dihydrosiloxane by the sequential hydrosilylation of two different unsaturated precursors. The process comprises (a) combining one equivalent of a polysiloxane with one to two equivalents of a first unsaturated precursor at 20° to 85° in the presence of a platinum, palladium, rhodium, iridium, iron, cobalt or nickel catalyst to produce a monohydrosiloxane; and (b) combining the monohydrosiloxane with an excess of a second unsaturated precursor at 85° to 200° in the presence of a platinum, palladium, rhodium, iridium, iron, cobalt or nickel catalyst to produce an unsymmetrical siloxane. As before, the preferred catalyst is a rhodium catalyst, most preferably tris(triphenylphosphine)rhodium (I) chloride. It is particularly surprising that the process is highly selective when the substrate is a siloxane of formula

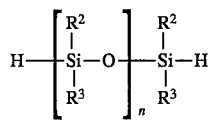

wherein n is zero, one and 3 to 100.

In another aspect, the invention relates to useful compounds produced by the process of the invention, namely, Compounds of formula I

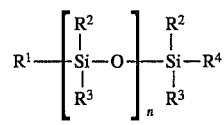

wherein $R^1$ is —CH=CHR$^5$, —CH$_2$CH$_2$R$^5$,

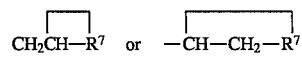

$R^2$ and $R^3$, are independently alkyl, fluoroalkyl, aryl or alkoxy;

$R^4$ is —CH=CHR$^6$, —CH$_2$CH$_2$R$^6$,

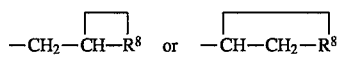

$R^5$ and $R^6$ are independently chosen from the group consisting of hydrogen, hydroxy, trialkoxysilyl, cyano, carboxy, carboxyalkyl, haloacyl, formyl, sulfonyl, alkyl, aryl and alkyl or aryl substituted with one or more substituents chosen from the group consisting of epoxides, alcohols, trialkoxysilanes, trihalosilanes, nitriles, carboxylic acids, esters, acyl halides, anhydrides, amines, aldehydes, sulfonic acids, sulfones, sulfoxides, oxetanes, lactones and vinyl ethers;

$R^7$ and $R^8$ are independently residues making up an epoxide-containing carbocycle of ring size 5 to 8;

n is an integer from 1 to 100;

$R^1$ and $R^4$ are different; and when n is two or greater, $R^1$ may additionally be hydrogen.

The compounds wherein at least one of $R^5$ and $R^6$ contains an epoxide, oxetane, acrylate ester, vinyl ether, or olefin are useful as monomers which can be polymerized to form coatings, adhesives and lubricants.

Alkyl as used herein refers to linear, branched or cyclic hydrocarbon residues of one to twenty carbons. Throughout this document the substituents are defined when introduced and retain that definition in all subsequent presentations.

In one series of compounds $R^1$ is hydrogen and n is from 2 to 100. These compounds are useful as intermediates in the synthesis of monomer units for silicone polymers. Preferred compounds of this series are those in which $R^2$ and $R^3$ are methyl, ethyl or trifluoropropyl, $R^4$ is CH$_2$CH$_2$R$^6$, $R^6$ is chosen from the group consisting of

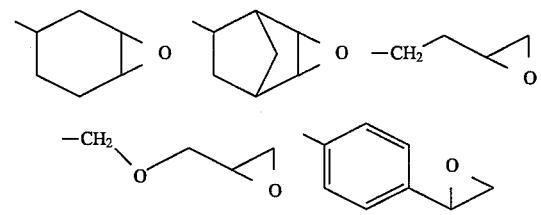

, and n is from 2 to 4. Particularly preferred are compounds II and III;

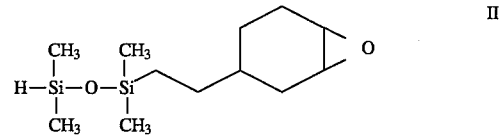

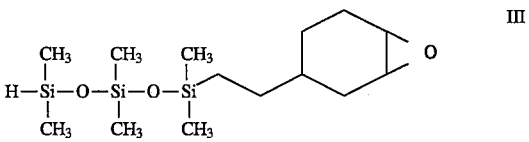

Other preferred compounds in this series are those in which $R^4$ is chosen from the group consisting of

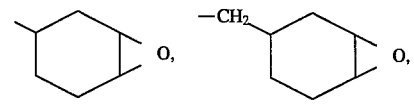

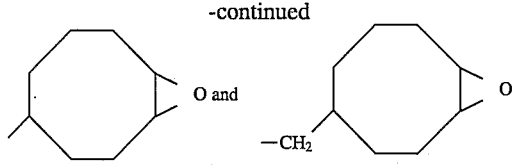

In a second series of such compounds $R^1$ is —CH$_2$CH$_2$R$^5$. These compounds are useful as monomer units for the production of silicone polymers for coatings, adhesives, and lubricants. Preferred compounds of this series are those in which $R^4$ is as above and $R^5$ and $R^6$ are chosen from the group consisting of trialkoxysilanes and alkyl epoxides. The epoxides are particularly useful in cationic polymerization reactions to produce cross-linked silicones.

Preferred species are those of formulas IV, V, and VI

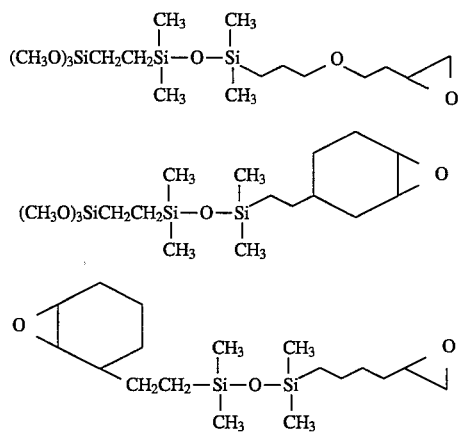

In another aspect the invention relates to a further series of useful compounds produced by the process of the invention:

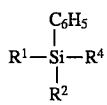

DETAILED DESCRIPTION OF THE INVENTION

The process of the invention is shown in general form in Scheme A:

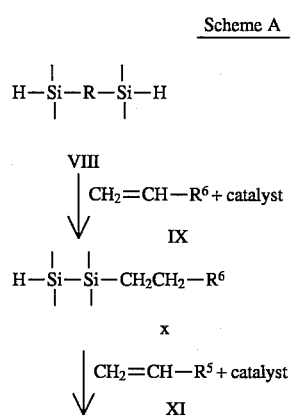

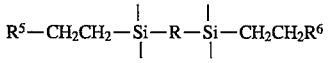

XII

In this general scheme a dihydrosiloxane having some residue, R, between the Si—H groups is reacted with an olefin IX to produce, selectively and with little or no byproduct containing two residues of IX, a silane X having a residual Si—H group at one terminus. The reaction is illustrated for simplicity with a terminal olefin IX or XI. However, it is not necessary to use a terminal olefin of that structure; acetylenes and olefins having exocyclic methylenes will also function in the process. Even internal olefins will function, albeit more sluggishly. The term "unsaturated" in this disclosure encompasses all of the foregoing groups of carbon-carbon double and triple bonds.

Hydrosilylation catalysts useful in this invention include chloroplatinic acid, Lamoreaux's platinum-octanol catalyst (U.S. Pat. No. 3,220,972), Ashby's platinum alkene catalyst (U.S. Pat. No. 3,159,601), Karstedt's platinum vinylsiloxanes (U.S. Pat. No. 3,715,334), tris(triphenylphosphine)rhodium chloride, dicobalt octacarbonyl, iron pentacarbonyl, bis(tri-phenylphosphine)palladium dichloride or diacetate, bis(acetylacetonato)nickel with triphenylphosphine, and copper (I) chloride ethylenediamine complexes. Preferred catalysts are complexes of rhodium, platinum, palladium and nickel such as bis(cyclooctadiene)rhodium chloride, bis(triphenylphosphine)nickel dichloride, bis(triphenylphosphine) palladium diacetate, and chloroplatinic acid. A particularly preferred catalyst is Wilkinson's catalyst, (Ph$_3$P)$_3$RhCl, or a polymer bound Wilkinson's catalyst. Catalysts that employ or generate colloidal platinum or palladium are to be avoided as they give rise to undesirable side reactions when $R^5$ or $R^6$ contains an epoxide.

The amount of catalyst can be in the range of about 5 to about 10,000 parts per million (ppm) by weight based on the weight of the elastomer. The preferred amount of catalyst is in the range of about 20 to about 1000 ppm.

The reactions may be run in hydrocarbon solvents, particularly toluene, in halogenated hydrocarbons or even in ethers such as dioxane or ethylene glycol dimethyl ether. In some cases the reactions may be carried out in the absence of solvent, but they are more difficult to control. Selective monosubstitution requires that the temperature be kept below about 85° C., and in exothermic reactions, such as most hydrosilylations, this is more easily achieved by running them at higher dilution.

The starting materials, dihydro(polysiloxanes), are readily available by procedures well-known in art, (see U.S. Pat. No. 5,097,054) and many are commercially available. The mechanism by which only one of two apparently equivalent Si—H bonds reacts is not clear. If the reaction did not distinguish between Si—H bonds, one would expect a statistical distribution of products. In the case where there is only one equivalent of olefin per two Si—H groups, a statistical distribution would yield a product mix of 25% unreacted, 50% mono-adduct and 25% di-adduct. Since the yields we have observed are routinely greater than 80% monoadduct with undetectable levels (less than 5%) of diadduct, there is clearly a high degree of selectivity in the process of the invention. Because the distance between reacting centers can be more than four bonds, it seems unlikely that the effect is electronic.

The postulation of a cyclic intermediate predicts that only when R (in formula VIII) is a two or three atom residue would there be any distinction between hydrogens. Since we have shown that the reaction works when R is a single atom (e.g., II) or when R is more than four atoms, this hypothesis cannot hold. Whatever the mechanism, it is very surprising that as much as two equivalents of unsaturated component can be present, and as long as the temperature is kept below about 85° only one of two Si—H groups more than 5 bonds apart will react. Apparently, the first addition and the second addition on the same molecule are widely separated kinetically and thermodynamically regardless of their spatial separation.

The products X are extremely valuable materials because they can be further elaborated into all sorts of asymmetric silanes, XII which can be used as monomers in polymerization reactions.

EXAMPLES

The examples given below were chosen for the purposes of illustration of this invention and are not in any way to be considered indicative of its limitations.

1-[2-[3-(7-Oxabicyclo[4.1.0]he-ptyl)]ethyl]-1,1,3,3-tetramethyldisiloxane (II)

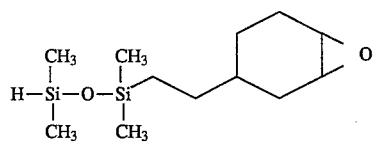

The synthetic procedures given below for 1-[2-[ 3-(7-Oxabicyclo[4.1.0]heptyl)]ethyl]-1,1,3,3tetramethyldisiloxane (II) are typical for those used for all α-hydrogen-ω-epoxy silanes.

Procedure A

A solution of 13.65 g (0.1 mol) 1,1,3,3-tetramethyldisiloxane and 6.20 g (0.05 mol) 3-vinyl- 7-oxabicyclo[4.1.0] heptane in 80 mL toluene were placed in a 250 mL round bottom flask equipped with a magnetic stir bar and a reflux condenser. To the solution there was added 1–2 drops of the Karstedt platinum catalyst. The reaction mixture was heated to 50–55° C. for 3 hr and then cooled to room temperature. Approximately 5 mg of 2-mercaptobenzothiazole was added to deactivate the hydrosilylation catalyst and the solvent and unreacted starting material removed in vacuo. There was obtained 12.4 g crude product (95% yield). The product was purified by fractional distillation with the desired monoepoxide boiling at 65° C. at 0.03 mm Hg (6.9 g, 56% yield).

Procedure B

To a 250 mL round bottom flask containing 40.2 g (0.3 mol) 1,1,3,3-tetramethyldisiloxane and 24.8 g (0.2 mol) 3-vinyl-7-oxabicyclo[4.1.0]heptane there was added 80 mL toluene. The reaction flask was equipped with a magnetic stirrer and a reflux condenser. To this solution was added approximately 5 mg chlorotris(triphenylphosphine) rhodium (I) as a catalyst and the reaction mixture heated to 80°–85° C. for 6 hr. The reaction was followed by gas chromatography by monitoring the disappearance of the starting materials and the appearance of the product. Next the solvent and any trace amounts of starting materials were removed through the use of a rotary evaporator yielding 51.10 g (99% yield based on the starting epoxide) of nearly pure product (by GLC). Fractional distillation gave the pure product (44.38 g, 86% isolated yield) with a boiling point of 65° C. at 0.03 mm Hg.

By a procedure analogous to that of procedure B of the previous example the following monohydrosiloxanes were synthesized from the corresponding dihydrosiloxane and olefin:

TABLE 1

| | STRUCTURE | Yield (%) | Boiling Point |
|---|---|---|---|
| III | H—Si(CH₃)₂—O—Si(CH₃)₂—O—Si(CH₃)₂—(cyclohexyl epoxide) | 99 | 65–68/0.03 |
| XIII | H—Si(CH₃)₂—O—(Si(CH₃)₂—O)₂—Si(CH₃)₂—(cyclohexyl epoxide) | 95 | 75–77/0.03 |
| XIV | H—Si(CH₃)₂—O—Si(CH₃)₂—(chain with epoxide) | 90 | 40–45/0.3 |
| XV | H—Si(CH₃)₂—O—Si(CH₃)₂—(longer chain with epoxide) | 86 | 45–48/0.3 |
| XVI | H—Si(CH₃)₂—O—Si(CH₃)₂—(chain with ether and epoxide) | 90 | 55–60/0.03 |

TABLE 1-continued

| STRUCTURE | Yield (%) | Boiling Point |
|---|---|---|
| XVII  H—Si(CH₃)₂—O—Si(CH₃)₂—CH₂CH₂—[cyclohexane]—O (epoxide) | 99 | 50–55/0.03 |
| XVIII  H—Si(CH₃)(C₆H₅)—CH₂CH₂CH₂CH₂—[cyclohexane]—O (epoxide) | 99 | 65–68/0.03 |
| XXI  H—Si(C₆H₅)₂—CH₂CH₂—[cyclohexane]—O (epoxide) | | |

Unsymmetrical Diepoxide (VI)

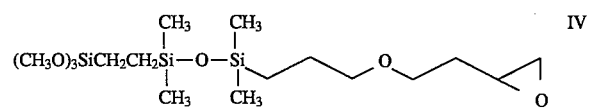

VI

Synthesis of 1-[2-[3-[7-Oxabicyclo[4.1.0]heptyl)]ethyl]-3-[2-trimethoxysilylethyl]-1,1,3,3-tetramethyldisiloxane (V)

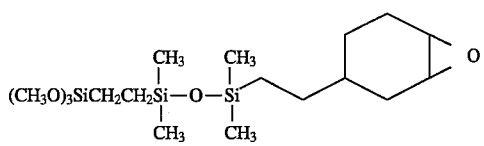

V

There were condensed together 2.58 g (0.01 mol) 1-[2-[3-[7-oxabicyclo[4.1.0]heptyl)]ethyl] tetramethyldisiloxane (II) and 1.8 g vinyltrimethoxysilane (0.012 mol) in the Combined into a 50 mL round bottom flask equipped as described above were 2.58 g 1-[2-[3(7-oxabicyclo[ 4.1.0] heptyl)]ethyl]-1,1,3,3tetramethyldisiloxane (II) (0.01 mol) prepared as described in procedure B and 1.2 g (0,012 mol) 1,2-epoxy- 5-hexene and approximately 3 mg of polymer bound Wilkinson's catalyst. The mixture was heated at 80°–85° C. until the band at 2120–2130 cm⁻¹ in the infrared had disappeared (7 hours). The reaction mixture was cooled to room temperature, the catalyst was removed by filtration, and the excess starting materials were removed in vacuo. There were isolated 3.2 g (90% yield) of the desired product.

When a solution of the above diepoxide containing 1% of the photoinitiator, (4-octyloxyphenyl)phenyliodonium hexafluoroantimonate, was spread as a 1 mil film and irradiated using a General Electric H3T7 medium pressure mercury arc lamp ballasted at 200 W, the film cured to a hard, transparent film within ten seconds. This film is useful as a protective and decorative coating for metals, plastics and glass.

presence of 3 mg polymer bound Wilkinson's catalyst. After 6 hours at 80–85° C. no absorption at 2160 cm⁻¹ in the infrared was noted and the reaction terminated. The reaction mixture was worked up in an identical manner as described in the previous experiment. There were isolated 3.32 g of the desired product in 82% over all yield.

Synthesis of 1-Glycidyloxypropyl-3trimethoxysilylethyl] tetramethyldisiloxane (IV)

(CH₃O)₃SiCH₂CH₂Si(CH₃)₂—O—Si(CH₃)₂—CH₂CH₂CH₂—O—CH₂—[epoxide]   IV

There were combined together into the usual experimental apparatus, 1.34 g (0.01 mol) 1,1,3,3-tetramethyldisiloxane, 1.34 g (0.01 mol) allylglycidyl ether and 40 mL toluene. To this mixture were added 1–2 drops of the Karstedt catalyst and the reaction heated at 55°–60° C. for 6 hr. Then 1.8 g (0.012 mol) vinyltrimethoxytrimethoxysilane was added and reaction continued for an additional 6 hr. Activated carbon was added to the reaction mixture and the solution was stirred and filtered. The solvent and unreacted starting materials were removed in vacuo leaving 3.4 g (84% yield) of the desired product as a colorless oil.

By a procedure analogous to that of the foregoing example, the following asymmetrical siloxanes were prepared from the corresponding dihydrosiloxane and olefins:

TABLE 2

| | | Yield |
|---|---|---|
| XXII | (CH₃O)₃Si—⟨⟩—Si(CH₃)—(O—Si(CH₃))₂—⟨⟩—cyclohexene oxide | 92 |
| XXIII | (CH₃O)₃Si—⟨⟩—Si(CH₃)—(O—Si(CH₃))₃—⟨⟩—cyclohexene oxide | 98 |
| XXIV | (CH₃O)₃Si—⟨⟩—Si(CH₃)—O—Si(CH₃)—⟨⟩—cyclohexene oxide | 80 |
| | (CH₃O)₃Si—⟨⟩—Si(CH₃)—O—Si(CH₃)—(CH₂)ₙ—epoxide | 89 |

While the invention has been particularly shown and described with reference to preferred embodiments thereof, it will be understood by those skilled in the art that other changes in form and details may be made therein without departing from the spirit and scope of the invention.

We claim:

1. A compound of formula

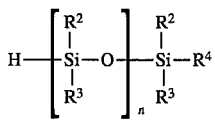

wherein $R_2$ and $R_3$, are independently alkyl, fluoroalkyl, aryl or alkoxy;

$R^4$ is —CH=CHR$^6$, —CH$_2$CH$_2$R$^6$,

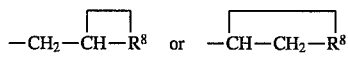

$R^6$ is chosen from the group consisting of alkyl or aryl substituted with one or more substituents chosen from the group consisting of epoxides, alcohols, trialkyoxysilanes, trihalosilanes, nitriles, carboxylic acids, esters, acyl halides, anhydrides, amines, aldehydes, sulfonic acids, sulfones, sulfoxides, oxetanes, lactones and vinyl ethers, with the proviso that $R^4$ must contain a polymerizable epoxide, oxetane, acrylate ester, vinyl ether or olefin;

$R^8$ is a residue making up an epoxide-containing carbocycle of ring size 5 to 8; and n is an integer from 1 to 100.

2. A compound of formula

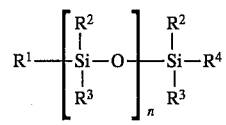

wherein $R^1$ is —CH=CH$^5$, —CH$_2$CH$_2$R$^5$,

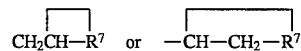

$R^2$ and $R_3$, are independently alkyl, fluoroalkyl, aryl or alkoxy;

$R^4$ is —CH=CHR$^6$, —CH$_2$CH$_2$R$^6$,

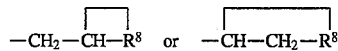

$R^5$ and $R^6$ are independently alkyl or aryl substituted with one or more substituents chosen from the group consisting of epoxides, alcohols, trialkyoxysilanes, trihalosilanes, nitriles, carboxylic acids, esters, acyl halides, anhydrides, amines, aldehydes, sulfonic acids, sulfones, sulfoxides, oxetanes, lactones and vinyl ethers, with the proviso that both of $R^5$ and $R^6$ must contain a polymerizable epoxide, oxetane, acrylate ester, vinyl ether or olefin;

$R^7$ and $R^s$ are independently residues making up an epoxide-containing carbocycle of ring size 5 to 8;

n is an integer from 1 to 100; and $R^1$ and $R^4$ are different.

3. A compound according to claim 1 wherein $R^2$ and $R^3$ are methyl, ethyl or trifluoropropyl.

4. A compound according to claim 1 wherein $R^4$ is CH$_2$CH$_2$R$^6$.

5. A compound according to claim 4 wherein $R^6$ is chosen from the group consisting of

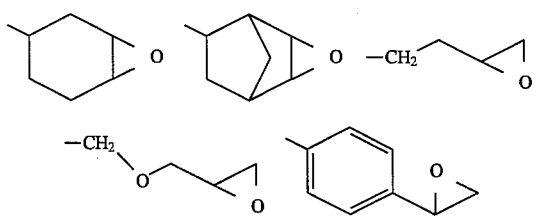

6. A compound according to claim 5 wherein n is from two to four.

7. A compound of formula

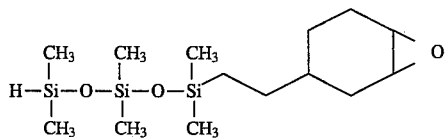

according to claim 6.

8. A compound according to claim 3 wherein $R^4$ is chosen from the group consisting of

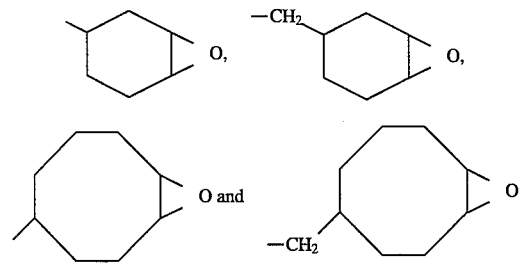

9. A compound according to claim 2 wherein $R^1$ is —CH$_2$CH$_2$R$^5$.

10. A compound according to claim 9 wherein $R^4$ is —CH$_2$CH$_2$R$^6$.

11. A compound according to claim 10 wherein $R^6$ is chosen from the group consisting of

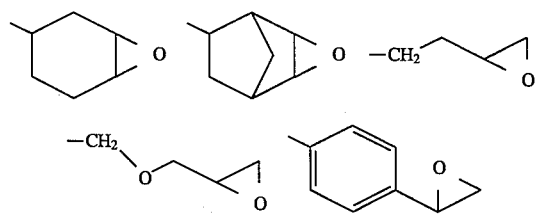

12. A compound according to claim 9 wherein $R^4$ is chosen from the group consisting of

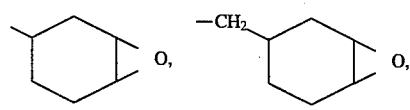

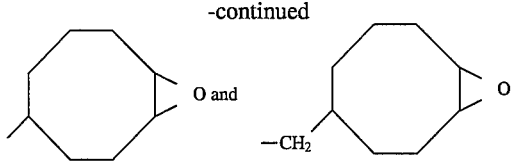

13. A compound according to claim 10 wherein $R^5$ and $R^6$ are alkyl epoxides.

14. A compound of formula

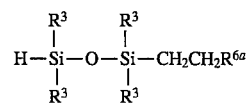

wherein
$R^3$ is alkyl, fluoroalkyl, aryl or alkoxy; and
$R^{6a}$ is an alkyl epoxide.

15. A compound of formula

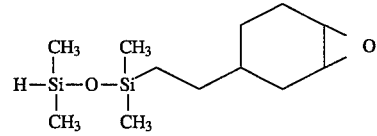

according to claim 14.

16. A compound of formula

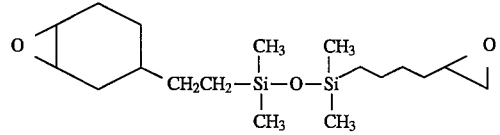

VI according to claim 13.

17. A compound of formula $$R^1-\underset{\underset{R^2}{|}}{\overset{\overset{C_5H_5}{|}}{Si}}-R^4$$

wherein $R^1$ is hydrogen, —CH=CHR$^5$, —CH$_2$CH$_2$R$^5$,

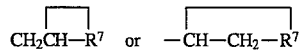

$R^2$ and $R_3$, are independently alkyl, fluoroalkyl, aryl or alkoxy;

$R^4$ is —CH=CHR$^6$, —CH$_2$CH$_2$R$^6$,

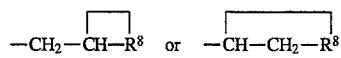

$R^5$ and $R^6$ are independently alkyl or aryl substituted with one or more substituents chosen from the group consisting of epoxides, alcohols, trialkyoxysilanes, trihalosilanes, nitriles, carboxylic acids, esters, acyl halides, anhydrides, amines, aldehydes, sulfonic acids, sulfones, sulfoxides, oxetanes, lactones and vinyl ethers, with the proviso that both of $R^5$ and $R^6$ must contain a polymerizable epoxide, oxetane, acrylate ester, vinyl ether or olefin;

$R^7$ and $R^8$ are independently residues making up an epoxide-containing carbocycle of ring size 5 to 8; and $R^1$ and $R^4$ are different.

18. A process for selectively reacting one equivalent of an olefin or acetylene with a hydrosiloxane having two silicon-hydrogen bonds, said process producing less than 5% of a product incorporating two moles of said olefin or acetylene, said process comprising combining one equivalent of a polysiloxane of formula

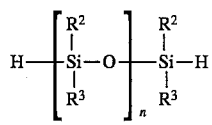

wherein $R^2$ and $R^3$ are independently alkyl, fluoroalkyl, aryl or alkoxy and n is zero, one or 3 to 100 with one to two equivalents of said olefin or acetylene at 20° to 85° in the presence of a rhodium catalyst.

19. A process according to claim 18 wherein said rhodium catalyst is a tris(triphenylphosphine)rhodium (I) chloride catalyst.

20. A process for producing an unsymmetrically substituted siloxane from a dihydrosiloxane by the sequential hydrosilylation of two different unsaturated precursors, said process comprising (a) combining one equivalent of a polysiloxane of formula

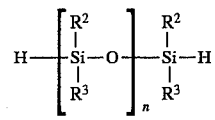

wherein $R^2$ and $R^3$ are independently alkyl, fluoroalkyl, aryl or alkoxy and n is zero, one or 3 to 100 with one to two equivalents of a first unsaturated precursor at 20° to 85° in the presence of a rhodium catalyst to produce a monohydrosiloxane; (b) combining said monohydrosiloxane with an excess of a second unsaturated precursor at 85° to 200° in the presence of a platinum, palladium, rhodium, iridium, iron, cobalt or nickel catalyst to produce an unsymmetrical siloxane.

21. A process according to claim 20 wherein said rhodium catalyst is a tris(triphenylphosphine)rhodium (I) chloride catalyst.

* * * * *

UNITED STATES PATENT AND TRADEMARK OFFICE
CERTIFICATE OF CORRECTION

PATENT NO. : 5,484,950
DATED : Jan. 16, 1996
INVENTOR(S) : Crivello

It is certified that error appears in the above-indentified patent and that said Letters Patent is hereby corrected as shown below:

Column 12, line 64, delete --claim 1-- and insert therefor "claim 3".

Signed and Sealed this

Eighteenth Day of June, 1996

Attest:

BRUCE LEHMAN

Attesting Officer        Commissioner of Patents and Trademarks